United States Patent
Crews

(10) Patent No.: US 11,045,904 B2
(45) Date of Patent: Jun. 29, 2021

(54) SURGICAL CANNULAS AND METHODS OF MANUFACTURING SURGICAL CANNULAS

(71) Applicant: Intuitive Surgical Operations, Inc., Sunnyvale, CA (US)

(72) Inventor: Samuel T. Crews, Palomar Park, CA (US)

(73) Assignee: INTUITIVE SURGICAL OPERATIONS, INC., Sunnyvale, CA (US)

(*) Notice: Subject to any disclaimer, the term of this patent is extended or adjusted under 35 U.S.C. 154(b) by 640 days.

(21) Appl. No.: 14/818,063

(22) Filed: Aug. 4, 2015

(65) Prior Publication Data
US 2016/0038237 A1 Feb. 11, 2016

Related U.S. Application Data

(60) Provisional application No. 62/035,142, filed on Aug. 8, 2014.

(51) Int. Cl.
*B23K 26/22* (2006.01)
*A61B 17/34* (2006.01)
(Continued)

(52) U.S. Cl.
CPC .......... *B23K 26/22* (2013.01); *A61B 17/3421* (2013.01); *B23K 31/02* (2013.01); *A61B 34/30* (2016.02); *A61B 2017/00526* (2013.01)

(58) Field of Classification Search
CPC ........ B23K 26/22; B23K 26/21; B23K 31/02; B23K 26/20; B23K 26/282;
(Continued)

(56) References Cited

U.S. PATENT DOCUMENTS

| 4,581,024 A | * | 4/1986 | Swenson | A61M 5/343 604/240 |
| 4,755,649 A | * | 7/1988 | Barker | B29C 66/12821 219/765 |

(Continued)

OTHER PUBLICATIONS

Custom 465® Stainless, Technical Datasheet [online], [retrieved on Dec. 4, 2012]. Retrieved from the Internet:< URL: http://cartech.ides.com/datasheet.aspx?i=101&E=55&FMT=PRINT>.

(Continued)

*Primary Examiner* — Kevin C Sirmons
*Assistant Examiner* — Alexandra Lalonde
(74) *Attorney, Agent, or Firm* — Jones Robb, PLLC

(57) ABSTRACT

A cannula includes a bowl portion with at least one depression in its outer surface, a tube portion, and a plurality of welds located at the at least one depression and joining the bowl portion to the tube portion. The plurality of welds may be discrete welds spaced from one another along a circumferential direction of the cannula. The weld joining a cannula bowl portion and a tube portion may be spaced from the distal end of the bowl portion. Various exemplary embodiments further contemplate methods of manufacturing a cannula by welding a tube portion and a bowl portion. Welding may occur, for example, in at least one depression of the bowl portion to form discrete welds spaced from one another along a circumferential direction of the cannula. In another example, welding may occur at a location spaced from and proximal to a distal end of the bowl portion.

23 Claims, 7 Drawing Sheets

(51) Int. Cl.
*B23K 31/02* (2006.01)
*A61B 17/00* (2006.01)
*A61B 34/30* (2016.01)

(58) Field of Classification Search
CPC ...... A61M 39/146; A61M 5/343; A61M 5/34; A61M 25/0014; A61M 5/349; A61M 25/0009; A61B 34/30; A61B 17/3421; A61B 19/00; B29C 65/04
See application file for complete search history.

(56) References Cited

U.S. PATENT DOCUMENTS

| | | | | |
|---|---|---|---|---|
| 5,315,993 | A * | 5/1994 | Alcala | A61B 5/14539 250/458.1 |
| 8,545,515 | B2 | 10/2013 | Prisco et al. | |
| 2006/0161114 | A1* | 7/2006 | Perot | A61F 9/0017 604/198 |
| 2011/0071541 | A1* | 3/2011 | Prisco | A61B 17/3421 606/130 |
| 2012/0165738 | A1* | 6/2012 | Harms | B23K 26/22 604/187 |
| 2012/0179114 | A1* | 7/2012 | Yokota | A61M 5/3293 604/239 |
| 2013/0325031 | A1 | 12/2013 | Schena et al. | |
| 2013/0325033 | A1 | 12/2013 | Schena et al. | |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

US 11,045,904 B2

1

SURGICAL CANNULAS AND METHODS OF MANUFACTURING SURGICAL CANNULAS

RELATED APPLICATIONS

This patent application claims priority to and the benefit of the filing date of U.S. Provisional Patent Application 62/035,142, entitled "SURGICAL CANNULAS AND METHODS OF MANUFACTURING SURGICAL CANNULAS," filed Aug. 8, 2014, which is incorporated by reference herein in its entirety.

TECHNICAL FIELD

Aspects of the present disclosure relate to surgical cannulas and methods of manufacturing such cannulas.

INTRODUCTION

Remotely controlled surgical instruments, which can include teleoperated surgical instruments (e.g., surgical instruments operated at least in part with computer assistance, such as instruments operated with robotic technology) as well as manually operated (e.g., laparoscopic, thorascopic) surgical instruments, are often used in minimally invasive medical procedures. During surgical procedures, a surgical instrument that extends through a cannula inserted into a patient's body can be remotely manipulated to perform a procedure at a surgical site. For example, in a teleoperated surgical system (e.g., robotic surgical system), cannulas and surgical instruments can be mounted at manipulator arms of a patient side cart and be remotely manipulated via teleoperation at a surgeon console.

In some teleoperated surgical procedures, a cannula is first manually inserted in a patient at a desired incision site and, once positioned, is docked to a mount on a patient side cart manipulator arm. Cannulas have been useful and effective for surgical procedures, but still further improvements upon cannulas and methods of manufacturing cannulas may be desirable.

SUMMARY

Exemplary embodiments of the present disclosure may solve one or more problems and/or may demonstrate one or more desirable features, which will become apparent from the description that follows.

In accordance with various exemplary embodiments, a cannula comprises a bowl portion including a distal section having at least one depression in an outer surface of the distal section, a tube portion, and a plurality of welds located at the at least one depression and joining the bowl portion to the tube portion, wherein the plurality of welds are discrete welds spaced from one another along a circumferential direction of the cannula.

In accordance with various exemplary embodiments, a cannula comprises a bowl portion and a tube portion comprising a proximal end region received in a distal end of the bowl portion, and further comprising a weld joining the bowl portion to the tube portion, wherein the weld is spaced from the distal end of the bowl portion.

In accordance with various exemplary embodiments, a method of manufacturing a cannula comprises inserting a tube portion into a distal section of a bowl portion, and welding the tube portion and the bowl portion to one another. The welding further comprises welding the tube portion and the distal section of the bowl portion to one another via a plurality of welds located at at least one depression of the bowl portion, wherein the plurality of welds are discrete welds spaced from one another along a circumferential direction of the cannula.

In accordance with various exemplary embodiments, a method of manufacturing a cannula comprises inserting a tube portion into a distal section of a bowl portion and welding the tube portion and the bowl portion to one another at a location spaced from and proximal to a distal end of the distal section.

Additional objects, features, and/or advantages will be set forth in part in the description which follows, and in part will be obvious from the description, or may be learned by practice of the present disclosure and/or claims. At least some of these objects and advantages may be realized and attained by the elements and combinations particularly pointed out in the appended claims.

It is to be understood that both the foregoing general description and the following detailed description are exemplary and explanatory only and are not restrictive of the claims; rather the claims should be entitled to their full breadth of scope, including equivalents.

BRIEF DESCRIPTION OF THE DRAWINGS

The present disclosure can be understood from the following detailed description, either alone or together with the accompanying drawings. The drawings are included to provide a further understanding of the present disclosure, and are incorporated in and constitute a part of this specification. The drawings illustrate one or more exemplary embodiments of the present teachings and together with the description serve to explain certain principles and operation.

DETAILED DESCRIPTION

Figure 1:
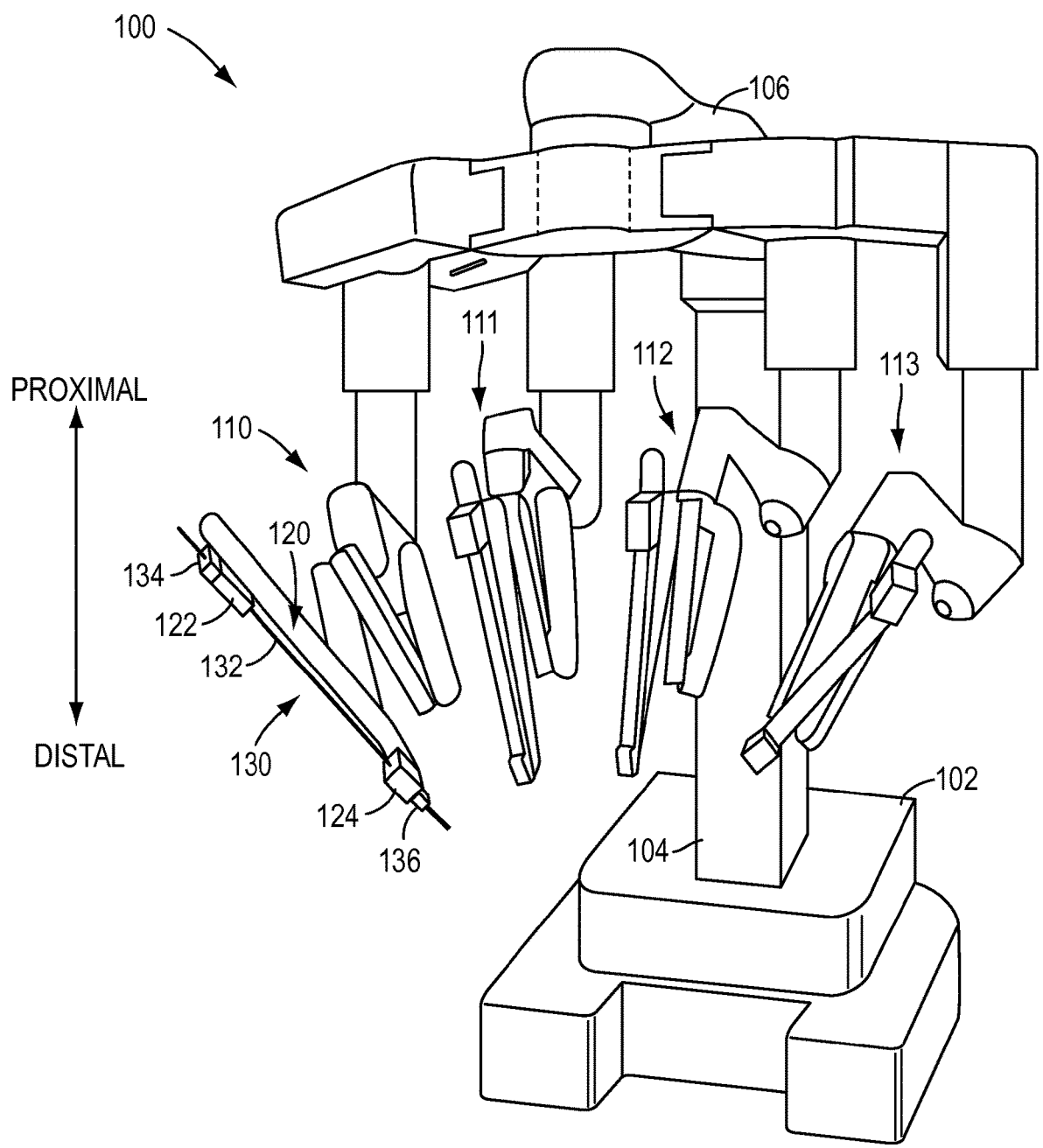
FIG. 1 is a perspective view of a patient side cart of a teleoperated surgical system, according to an exemplary embodiment.

This description and the accompanying drawings that illustrate exemplary embodiments should not be taken as limiting. Various mechanical, compositional, structural, electrical, and operational changes may be made without departing from the scope of this description and the claims, including equivalents. In some instances, well-known structures and techniques have not been shown or described in detail so as not to obscure the disclosure. Like numbers in two or more figures represent the same or similar elements. Furthermore, elements and their associated features that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment.

For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

Further, this description's terminology is not intended to limit the disclosure or claims. For example, spatially relative terms—such as "beneath", "below", "lower", "above", "upper", "proximal", "distal", and the like—may be used to describe one element's or feature's relationship to another element or feature as illustrated in the orientation of the figures. These spatially relative terms are intended to encompass different positions (i.e., locations) and orientations (i.e., rotational placements) of a device in use or operation in addition to the position and orientation shown in the figures. For example, if a device in the figures is inverted, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly. The relative proximal and distal directions of surgical instruments are labeled in the figures.

The present disclosure contemplates various surgical cannulas and methods of manufacturing such cannulas. Exemplary embodiments are directed to cannulas comprising a bowl portion and tube portion joined to one another such that stress transmitted through a cannula, such as from bowl portion to tube portion, are spread over a relatively large area, and a joint between the bowl portion and the tube portion is robust. The tube portion may be straight or may be curved. The bowl portion and tube portion are joined, such as via welding. According to an exemplary embodiment, laser welding is used to join the bowl portion and tube portion. A weld may be proximally spaced from a distal tip of a bowl portion along an axial direction (i.e., a proximal-distal direction) of a cannula, according to an exemplary embodiment. The bowl portion and tube portion may be joined by a plurality of discrete welds spaced apart from one another along a circumferential direction of a cannula, according to an exemplary embodiment. According to various exemplary embodiments, sections of the bowl portion between welds lack a heat affected zone from a welding process to join bowl portion and tube portion.

According to an exemplary embodiment, welds are located in depressions that have a reduced wall thickness of the bowl portion in comparison to parts of the bowl portion where depressions are not located (e.g., parts of bowl portion between, proximal to, and/or distal to the depressions). The bowl portion may have a plurality of discrete depressions spaced apart from one another along a circumferential direction of a cannula, according to an exemplary embodiment. Depressions and welds may have various shapes when viewed from above (i.e., not in cross section), such as, for example, a trapezoidal shape, elongated shape, elliptical shape, oval shape, circular shape, rectangular shape, square shape, or other shape. According to an exemplary embodiment, a bowl portion comprises a single, continuous circumferential depression including a plurality of welds or a single, continuous circumferential weld. The bowl portion and the tube portion may be configured to be press fit together when the bowl portion and the tube portion are assembled during manufacture of a cannula, according to an exemplary embodiment. According to various exemplary embodiments, the press fit facilitates the tube portion remaining connected to the bowl portion, even when a weld joining the bowl portion and the tube portion fails or material of the bowl portion and/or the tube portion within a heat affected zone (HAZ) adjacent to a weld fails.

Although the various exemplary embodiments described herein are discussed with regard to surgical instruments used with a patient side cart of a teleoperated surgical system, the various exemplary embodiments are not limited to use with surgical instruments for a teleoperated surgical system. For example, the various exemplary embodiments described herein may be used with hand-held, manual surgical instruments.

Referring now to FIG. 1, an exemplary embodiment of a patient side cart 100 of a teleoperated surgical system is shown. A teleoperated surgical system may further include a surgeon console (not shown) for receiving input from a user to control instruments mounted at patient side cart 100. A teleoperated surgical system also can include an auxiliary control/vision cart (not shown), as described in, for example, U.S. Pub. No. US 2013/0325033 A1, entitled "Multi-Port Surgical Robotic System Architecture" and published on Dec. 5, 2013, and U.S. Pub. No. US 2013/0325031 A1, entitled "Redundant Axis and Degree of Freedom for Hardware-Constrained Remote Center Robotic Manipulator" and published on Dec. 5, 2013, each of which is hereby incorporated by reference in its entirety. Further, the exemplary embodiments described herein may be used, for example, with a da Vinci® Surgical System, such as the da Vinci Si® Surgical System or the da Vinci Xi® Surgical System, both with or without Single-Site® single orifice surgery technology, all commercialized by Intuitive Surgical, Inc.

According to an exemplary embodiment, patient side cart 100 includes a base 102, a main column 104, and a main boom 106 connected to main column 104. Patient side cart 100 also includes a plurality of teleoperated manipulator arms 110, 111, 112, 113, which are each connected to main boom 106, as depicted in the exemplary embodiment of FIG. 1. Manipulator arms 110, 111, 112, 113 may each include an instrument mount portion 120 to which an instrument 130 may be mounted, which is illustrated as being attached to manipulator arm 110. Portions of manipulator arms 110, 111, 112, 113 may be manipulated during a surgical procedure according to commands provided by a user at the surgeon console. In an exemplary embodiment, signal(s) or input(s) transmitted from a surgeon console are transmitted to the control/vision cart, which interprets the input(s) and generate command(s) or output(s) to be transmitted to the patient side cart 100 to cause manipulation of an instrument 130 (only one such instrument being mounted in FIG. 1) and/or portions of manipulator arm 110 to which the instrument 130 is coupled at the patient side cart 100.

Instrument mount portion 120 may comprise an actuation interface assembly 122 and a cannula mount 124. A shaft 132 of instrument 130 extends through cannula mount 124 (and on to a surgery site during a surgical procedure). A force transmission mechanism 134 of instrument 130 is mechanically coupled with the actuation interface assembly 122, according to an exemplary embodiment. Persons skilled in the art will be familiar with surgical instrument force transmission mechanisms, which receive a mechanical input force from a source (e.g., an electric motor on a manipulator supporting the instrument) and convert and/or redirect the received force to an output force to drive a component (e.g., a wrist, and end effector) on the instrument. Cannula mount 124 may be configured to hold a cannula 136 through which shaft 132 of instrument 130 may extend to a surgery site during a surgical procedure. Actuation interface assembly 122 may contain a variety of drive and other mechanisms that are controlled to respond to input commands at the surgeon console and transmit forces to the force transmission mechanism 134 to actuate instrument 130, as those skilled in the art are familiar with.

Although the exemplary embodiment of FIG. 1 shows an instrument 130 attached to only manipulator arm 110 for ease of illustration, an instrument may be attached to any and each of manipulator arms 110, 111, 112, 113. An instrument 130 may be a surgical instrument with an end effector or may be an endoscopic imaging instrument or other sensing instrument used during a surgical procedure to provide information, (e.g., visualization, electrophysiological activity, pressure, fluid flow, and/or other sensed data) of a remote surgical site. In the exemplary embodiment of FIG. 1, a surgical instrument with an end effector or an imaging instrument may be attached to and used with any of manipulator arms 110, 111, 112, 113. However, the embodiments described herein are not limited to the exemplary embodiment of the patient side cart of FIG. 1 and various other teleoperated surgical system configurations, including patient side cart configurations, may be used with the exemplary embodiments described herein.

Figure 2:
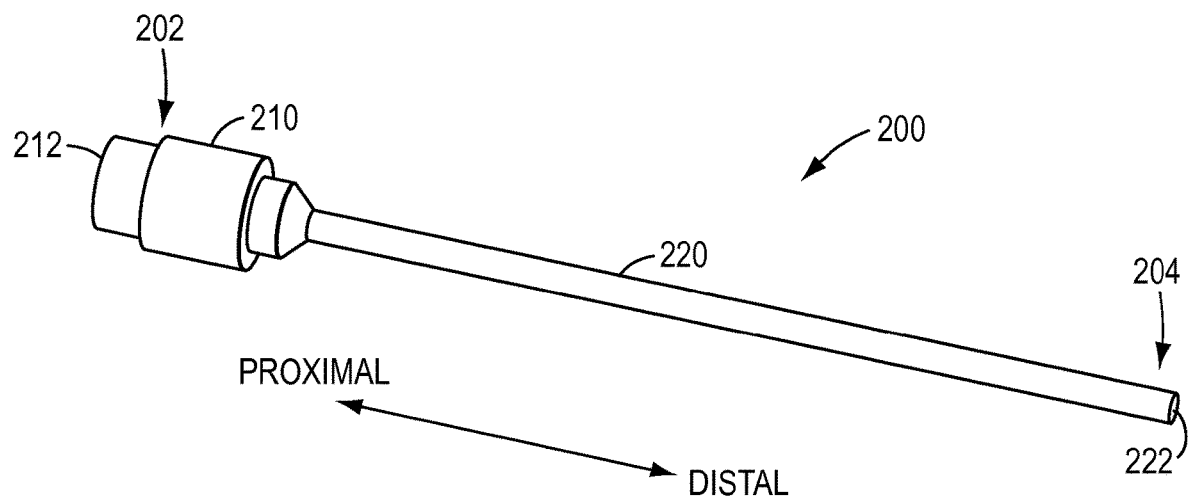
FIG. 2 is a perspective view of a cannula including a straight tube portion, according to an exemplary embodiment.

Turning to FIG. 2, a side view of an exemplary embodiment of a cannula 200 is shown. Cannula 200, as well as the various exemplary embodiments of cannulas described herein, may be used with the patient side cart 100 discussed above with regard to the exemplary embodiment of FIG. 1, as well as with other computer-assisted surgical systems or with manually-operated instruments. According to various exemplary embodiments, cannulas of the various exemplary embodiments described herein are configured to be connected to cannula mount 124 in a similar manner to cannula 136. As shown in the exemplary embodiment of FIG. 2, cannula 200 includes a bowl portion 210 and a tube portion 220. Bowl portion 210 is located at a proximal portion 202 of cannula 200 and tube portion 220 is located at a distal portion 204 of cannula 200. Bowl portion 210 may be, for example, the portion of cannula 200 connected to cannula mount 124 of patient side cart 100. As a result, shaft 132 of instrument 130 may be inserted into an opening 212 in bowl portion 210, through cannula 200, and out of distal opening 222 of tube portion 220 to a surgical site.

According to an exemplary embodiment, bowl portion 210 and tube portion 220 are each made of metal, such as, for example, a stainless steel alloy. For example, bowl portion 210 and tube portion 220 may each be made of a precipitation hardenable stainless steel. According to an exemplary embodiment, bowl portion 210 may be made of, for example, 17-4 stainless steel. According to an exemplary embodiment, tube portion 220 is made of an alloy having a composition of (in weight percentage): carbon about 0.02% maximum, phosphorous about 0.015% maximum, silicon about 0.25% maximum, nickel about 10.75% to about 11.25%, titanium about 1.50% to about 1.80%, manganese about 0.25% maximum, sulfur about 0.010% maximum, chromium about 11.00% to about 12.50%, molybdenum about 0.75% to about 1.25%, and balance iron, such as Custom® 465 stainless steel produced by Carpenter Technology Corporation of Reading, Pa.

Bowl portions and/or tube portions of cannulas of the exemplary embodiments described herein are not limited to metals, however, and may be made of other materials, such as, for example, plastics. For example, bowl portions and/or tube portions of cannulas can be made of, for example, polycarbonate, polyether ether ketone (PEEK), or other plastics used for surgical instruments. According to an exemplary embodiment, bowl portion 210 and tube portion 220 are made of different materials.

Tube portion 220 may be straight (e.g., have a straight longitudinal axis along its length), as shown in the exemplary embodiment of FIG. 2. However, the cannulas of the various exemplary embodiments described herein are not limited to cannulas with straight tube portions. As depicted in the exemplary embodiment of FIG. 4, a cannula 600 includes a bowl portion 610 and a tube portion 620. Tube portion 620 may be curved or include a curved portion 624 (e.g., at least a portion of the longitudinal axis along at least a portion of tube portion 620 is curved). Cannulas including a curved portion, such as cannula 600, may be configured according to the exemplary embodiments described in U.S. Pat. No. 8,545,515 (issued Oct. 1, 2013) (entitled "Curved Cannula Surgical System"), which is hereby incorporated by reference in its entirety. As described in U.S. Pat. No. 8,545,515, cannulas including a curved portion assist with providing a triangulation angle for an instrument inserted to a surgical site and enhance visibility of the surgical site, according to various exemplary embodiments.

Although various exemplary embodiments described and shown regard cannulas having curved tube portions, the scope of the present disclosure is not limited to such configurations, but also includes cannulas with straight tube portions. It should be appreciated that the scope of the present disclosure also encompasses cannulas that have compound curve configurations (e.g., two or more separate curved portions, either within the same plane or within different planes; a three-dimensional curved portion within a volume; and the like) and various other configurations.

Figure 3:
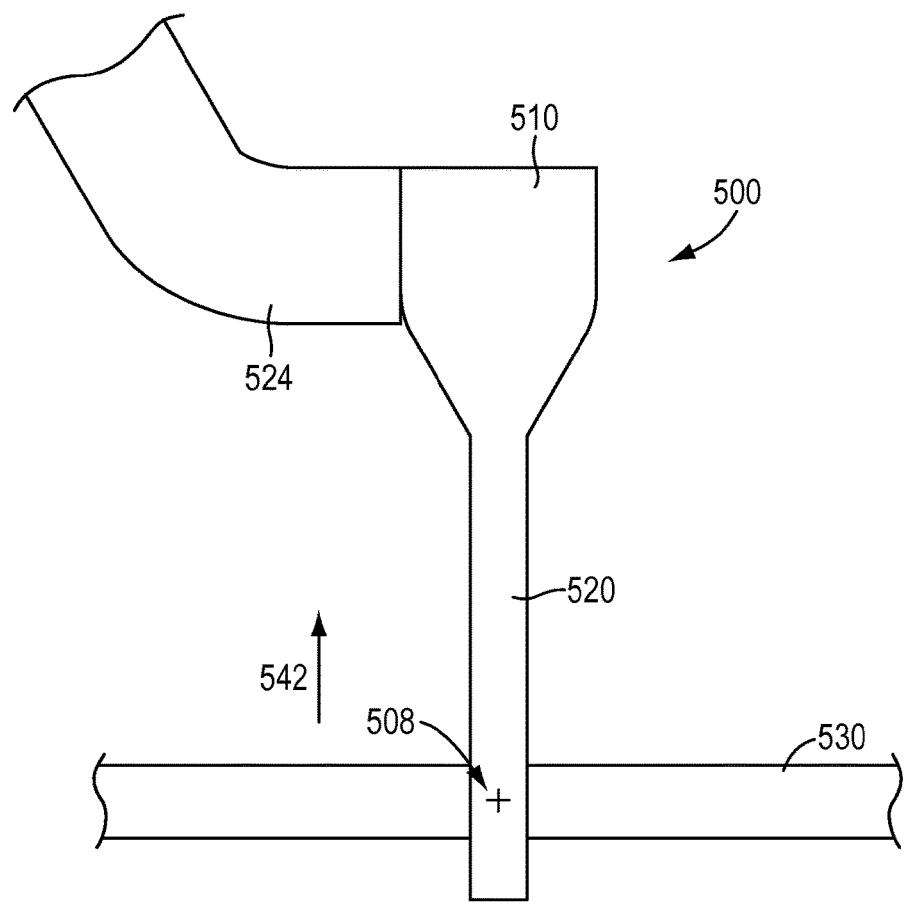
FIG. 3 is a partial side view of a cannula inserted into a body wall, according to another exemplary embodiment.

As described above, in use, cannulas in accordance with the present disclosure can be inserted into a body wall of a patient or through a natural orifice to perform a surgical procedure. As shown in the exemplary embodiment of FIG. 3, a cannula 500 is inserted in a body wall 530 of a patient. Cannula 500 includes a bowl portion 510 and tube portion 520 and may be configured according to the various exemplary embodiments described herein. According to an exemplary embodiment, cannula 500 is connected to a cannula mount of a patient side cart, such as cannula mount 124 of patient side cart 100 of the exemplary embodiment of FIG. 1. For instance, bowl portion 510 of cannula 500 may be connected to cannula mount 524 by arms (not shown in FIG. 3) of cannula mount 524 clamping about bowl portion 510 or by insertion of a projection (not shown in FIG. 3) into cannula mount 524.

In some cases, when multiple cannulas 500 are inserted through body wall 530, contact may occur between the cannulas. For instance, a surgeon may withdraw cannulas along proximal direction 542 in FIG. 3 in an attempt to achieve greater visibility of a surgical site, which in turn withdraws the remote center of motion 508 along direction 542 to a location beyond body wall 530. This withdrawal of the cannulas can lead to contact between the cannulas, such as when corresponding manipulator arms move each of the cannulas. For example, contact may occur between tube portions of the cannulas, which can induce stress in the cannulas, such as in the walls of the bowl portions and tube portions of the cannulas and in a weld joining the bowl portion and tube portion of a cannula. Such contact may transmit stresses from bowl portions of cannulas (which are each connected to a mount 524) to the tube portion, such as where those two components are joined or interact. In view of these considerations, it may be desirable to provide robust cannulas and methods of manufacturing the cannulas.

Figure 4:
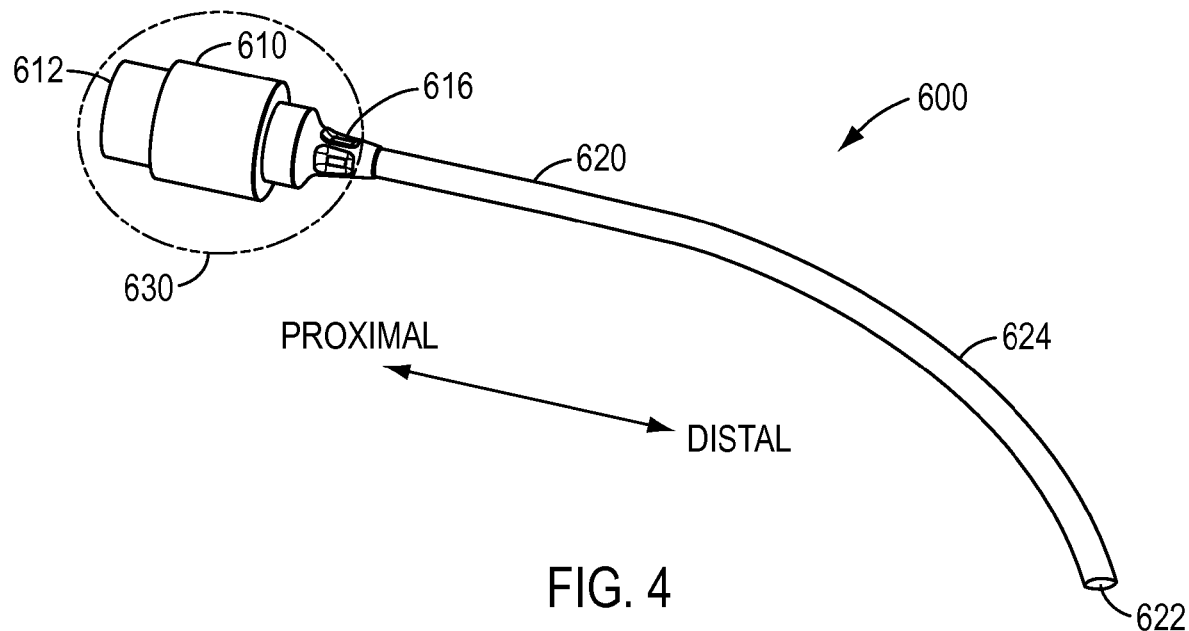
FIG. 4 is a perspective view of a cannula, according to an exemplary embodiment.

Turning to FIG. 4, a cannula 600 is depicted that includes a robust connection between its bowl portion 610 and tube portion 620. Bowl portion 610 includes a proximal opening 612 for insertion of a shaft 132 of instrument 130 through bowl portion 610, through tube portion 620, and out distal opening 622 of tube portion 620 to a surgical site, as discussed above with regard to the exemplary embodiment of FIG. 2. Bowl portion 610 and tube portion 620 may be made of the same materials as bowl portion 210 and tube portion 620, as discussed above with regard to the exemplary embodiment of FIG. 2. As shown in the exemplary embodiment of FIG. 4, tube portion 620 may include a curved portion 624. However, cannula 600 is not limited to curved tube portions and may instead include tube portions that are straight, as discussed above in regard to the exemplary embodiment of FIG. 2.

Figure 5:
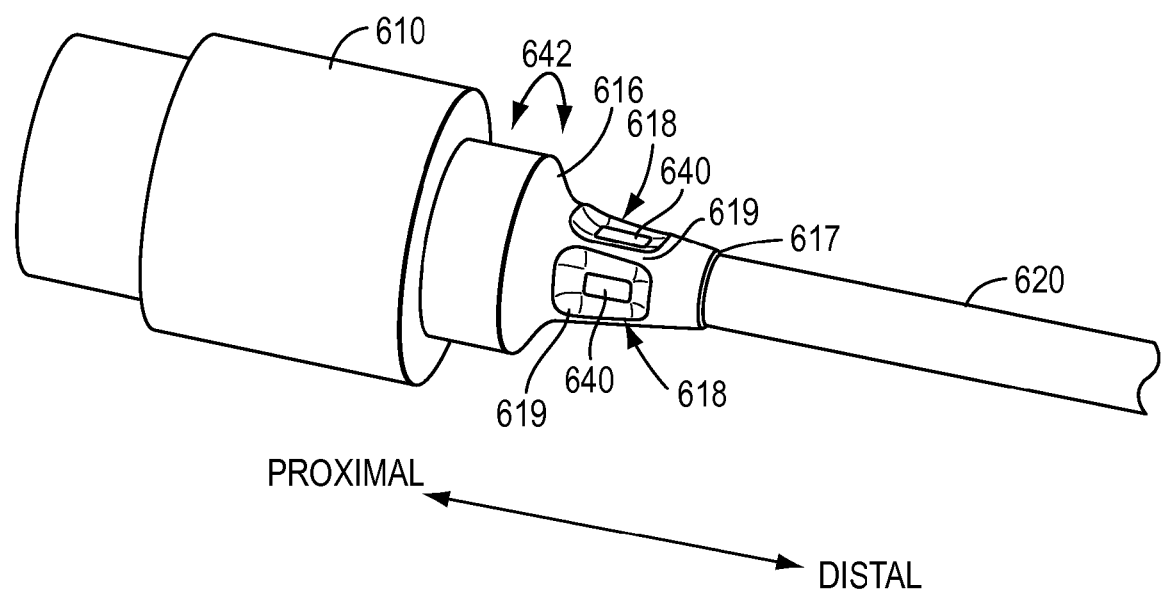
FIG. 5 is a partial perspective view of the bowl portion and part of the tube portion of the cannula of FIG. 4.

In various exemplary embodiments, a weld configuration used to join a bowl portion and a tube portion has a relatively high strength due to the geometry and/or location of the weld. FIG. 5 shows an enlarged view of area 630 of the exemplary embodiment of FIG. 4, which incorporates a weld configuration in accordance with various exemplary embodiments. As shown in the exemplary embodiment of FIG. 5, distal bowl section 616 includes one or more depressions 618 of reduced wall thickness in comparison to parts of distal bowl section 616 where depressions 618 are not located (e.g., parts of bowl section 616 between, proximal to, and/or distal to depressions 618). To join bowl portion 610 and tube portion 620, a weld 640 may be co-located with each depression 618, as shown in the exemplary embodiment of FIG. 5. For instance, a weld 640 may be located at a surface of a depression 618 where a wall thickness of distal bowl section 616 is reduced to facilitate welding. Thus, the weld configuration of the exemplary embodiment of FIGS. 4 and 5 can include a number of discrete welds 640 that are spaced apart in a circumferential direction 640 of bowl portion 610.

In an exemplary embodiment, as can be seen in FIGS. 4 and 5, welds 640 are positioned at approximately the same axial location (e.g., along a proximal-distal direction) along cannula 600. As a result of this configuration, non-welded material of bowl portion 610 and tube portion 620 form ribs 619 located between welds 640 along a circumferential direction 642 of cannula 600. By spacing welds 640 apart from one another, sections of distal bowl section 616 located between welds 640 remain unaffected by a welding process. For instance, sections of distal bowl section 616 located between welds 640 may lack a heat affected zone. Because heat affected zones can weaken the strength of a material, including sections that are not heat-affected can provide a robust weld to join a bowl portion and tube portion of a cannula. According to an exemplary embodiment, welds 640 are spaced about distal bowl section 616, such as along circumferential direction 642 in the exemplary embodiment of FIG. 5, to cover a portion of distal bowl section 616. For example, in combination, the welds 640 can cover a portion of the circumference of distal bowl section ranging from about 20 percent to about 70 percent. In various exemplary embodiments, the welds 640 may be placed at uniformly-spaced intervals in the circumferential direction 642, although non-uniform spacing between welds around the circumferential direction also is contemplated as being within the scope of the present disclosure.

Figure 6:
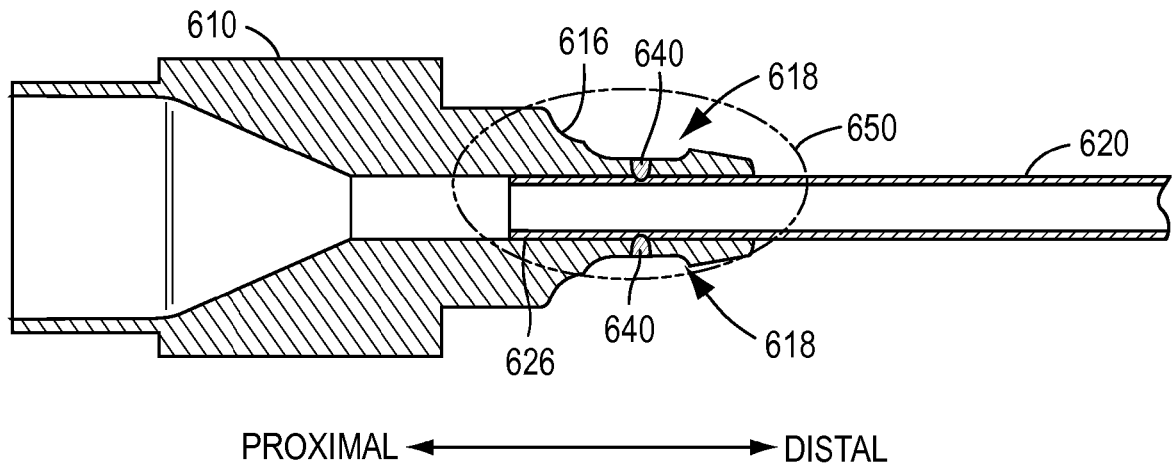
FIG. 6 is a cut-away view along a length of the cannula of FIG. 5.
Figure 7:
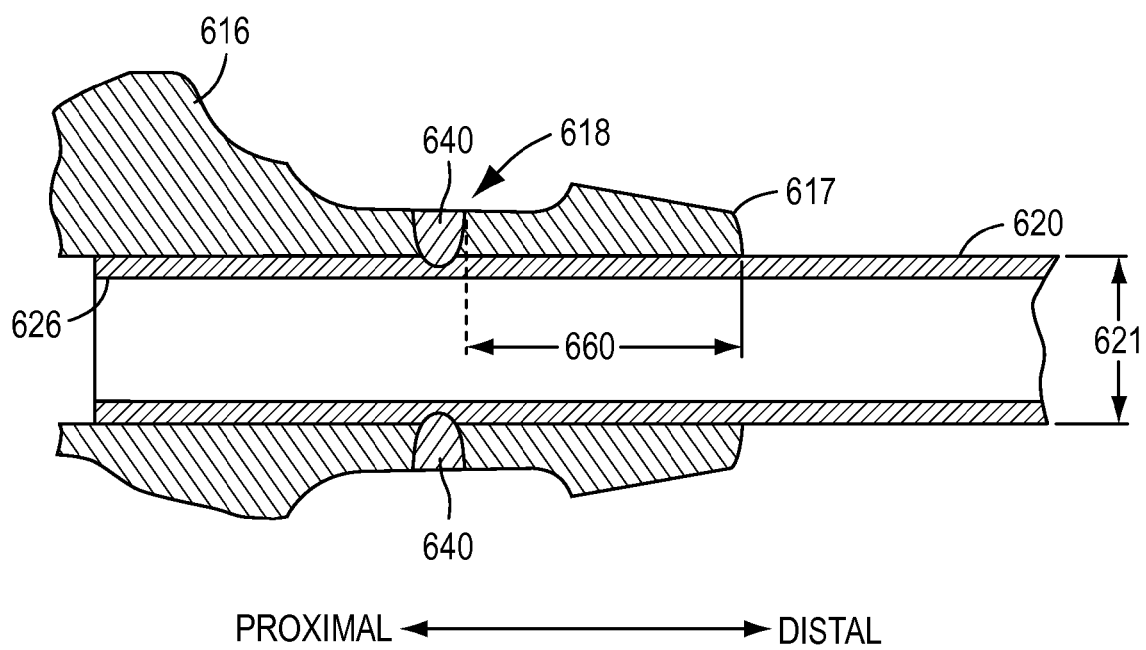
FIG. 7 is an enlarged view of an area 650 in FIG. 6.

As mentioned above, when a distal bowl section 616 includes depressions 618, a weld 640 may be located at a depression 618, as shown in FIG. 6. Weld 640 may be located distal to a proximal portion of tube portion 620 inserted within distal bowl section 616, as shown in FIG. 6. Turning to FIG. 7, an enlarged view of area 650 of FIG. 6 is shown which further illustrates details of weld 640 in the exemplary embodiments of FIGS. 4-7. As indicated in FIG. 7, weld 640 may be a penetration weld that completely penetrates through the wall of bowl distal portion 616 and through a portion of the wall of tube portion 620. According to an exemplary embodiment, weld 640 penetrates through, for example, about 10 percent to about 90 percent of a wall thickness of tube portion 620. According to another exemplary embodiment, weld 640 penetrates through, for example, about two-thirds of a wall thickness of tube portion 620. For example, when tube portion 620 has a wall thickness of about 0.008 inches to about 0.025 inches, weld 640 penetrates through about 0.0008 to about 0.022 inches of the wall thickness of tube portion 620. According to an exemplary embodiment, a radial thickness of distal bowl section 616 at the location of depression 618 may substantially match a wall thickness of tube portion 620.

As mentioned above, in instances of induced stress on a cannula, the bowl portion may transmit stresses to the tube portion, such as where those two components are joined or otherwise interact. With reference to FIG. 7, exemplary weld configurations described herein, including the exemplary embodiments of FIGS. 5 and 6, address this consideration by proximally spacing weld 640 a distance 660 from a distal tip 617 of distal bowl section 616 (e.g., along an axial proximal-distal direction of a cannula). According to an exemplary embodiment, a distance 660 from distal tip 617 of distal bowl section 616 to weld 640 (which may be a distance to a distal edge of weld 640, as shown in FIG. 7), may be approximately equal to or larger than the diameter 621 of the tube portion 620. For example, the distance 660 can be selected from within a range from about 1 to about 3 times the diameter 621 of tube portion 620. Each of welds 640 depicted in the exemplary embodiment of FIG. 5 may be configured according to the configuration shown in FIG. 7. As a result, welds 640 are situated at a location having lower stress than the stress that may occur at a location of the distal tip 617 of bowl section 616. In addition, the material of distal bowl section 616 at distal tip 617 is not subject to the weld process. For instance, the material of distal bowl section 616 at distal tip 617 does not include a heat affected zone, which weakens the material at distal tip 617.

Welds 640 may be formed by various welding processes, such as, for example, laser welding. According to an exemplary embodiment, laser welding is performed with a laser having a power in a range of, for example, from about 600 W to about 750 W. The various exemplary embodiments described herein are not limited to welds formed via laser welding, however, and may be formed by other welding processes, such as, for example tungsten inert gas (TIG) welding, metal inert gas (MIG) welding, resistance welding, friction welding, and other welding processes.

Figure 8:
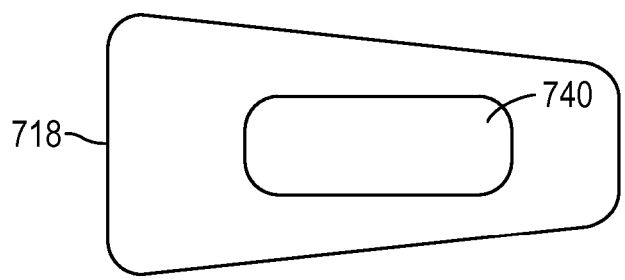
FIG. 8 is a top view of a depression and weld, according to an exemplary embodiment.
Figure 9:
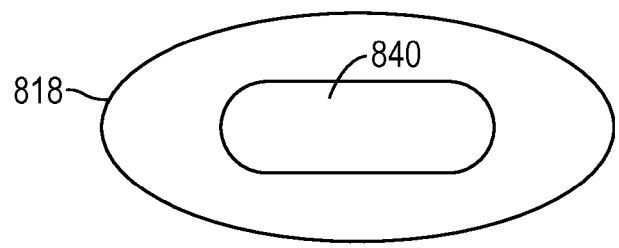
FIG. 9 is a top view of a depression and weld, according to another exemplary embodiment.
Figure 10:
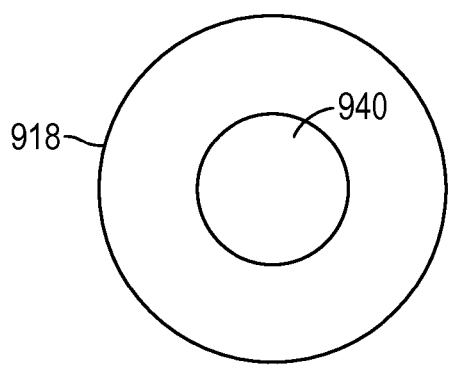
FIG. 10 is a top view of a depression and weld, according to another exemplary embodiment.

According to various exemplary embodiments, depressions in a distal bowl section of a cannula have a shape designed to facilitate welding a bowl portion and tube portion of the cannula together while providing a strong weld. A weld may have a shape designed to increase the area of the weld, and thus can distribute forces across a relatively large area of the weld. FIG. 8 shows a top view of a depression 718 with a weld 740 located within depression. Depression 718 has a trapezoidal shape, as shown in FIG. 8, and may be used in the distal bowl section of the various exemplary embodiments described herein. The shape of weld 740 may be controlled by the beam shape (e.g., cross-sectional shape of a laser beam used in the weld process) upon a cannula and/or the travel path of the laser beam when laser welding is utilized. As shown in the exemplary embodiment of FIG. 8, weld 740 may have a generally rectangular shape. However, the depressions and welds of the various exemplary embodiments described herein are not limited to the shapes depicted in FIG. 8 and may have other shapes. For instance, each of depression 818 and weld 840 may have a generally elongated, elliptical, or oval shape, as shown in the exemplary embodiment of FIG. 9. In another exemplary embodiment, each of depression 918 and weld 940 may have a generally circular shape, as shown in FIG. 10. The configurations depicted in FIGS. 8-10 are non-limiting and the present disclosure contemplates a variety of other shapes that may be used for depressions and welds, such as, for example, a generally square shape. The weld may fill the shape of the bottom of the depression, or the weld optionally fills only one or more portions of the shape of the bottom of the depression, or the weld optionally extends along the perimeter or a portion of the perimeter of the shape of the bottom of the depression.

The number of depressions may vary when a distal bowl section of a cannula includes depressions for welding. Distal bowl section 616 of the exemplary embodiment of FIG. 5 may include, for example, four depressions 618. The various exemplary embodiments described herein, however, are not limited to including four depressions and instead may include other numbers of depressions, such as, for example, one, two, three, five, six, seven, eight, or more depressions.

The size of a weld may be selected to distribute the stress applied to the weld. For example, a weld may have a cross-sectional size or area selected to maximize the distribution of stress transmitted to weld, such as due to forces applied to a tube portion of a cannula during a surgical procedure. According to an exemplary embodiment, a weld may have a cross-sectional area ranging from, for example, about 0.010 square inches to about 0.100 square inches.

A distal bowl section of a cannula may include structures to enhance the strength of the distal bowl section, such as near the location of one or more depressions. According to an exemplary embodiment, distal bowl section 616 in FIG. 5 may also include one or more longitudinal ribs 619 to enhance the strength of distal bowl section 616, such as, for example, enhancing the bending strength of the distal bowl section 616. For example, distal bowl section 616 may include a rib 619 between each depression 618, as indicated in the exemplary embodiment of FIG. 5.

Figure 11:
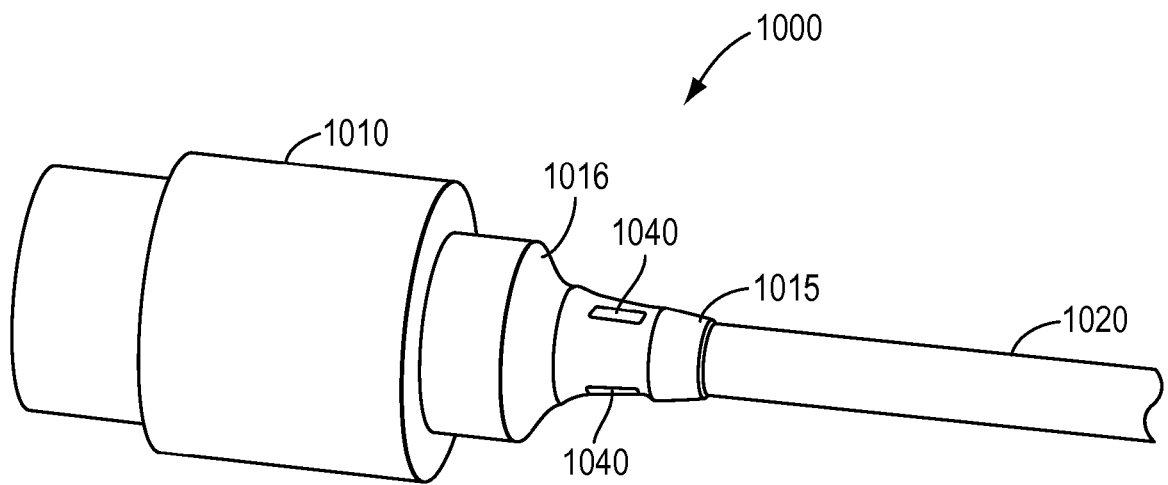
FIG. 11 is a perspective view of a cannula, according to another exemplary embodiment.

The various exemplary embodiments described herein are not limited to distal bowl sections including ribs, however, and may instead lack ribs. For example, a cannula 1000 may include a bowl portion 1010 and a tube portion 1020, as shown in the exemplary embodiment of FIG. 11. Bowl portion 1010 may include a distal bowl section 1016 having a circumferential section 1015 of reduced wall thickness (e.g., in comparison to parts of distal bowl section 1016 not including circumferential section 1015, such as parts of distal bowl section 1016 proximal and/or distal to circumferential section 1015) in which welds 1040 are located to join bowl portion 1010 and tube portion 1020. Circumferential section 1015 may have a similar wall thickness present at the bottom of depressions 618 of the exemplary embodiment of FIGS. 4-7 but without ribs 619 so that circumferential section 1015 is a continuous, circumferential band of reduced wall thickness where discrete welds 1040 may be located.

Figure 12:
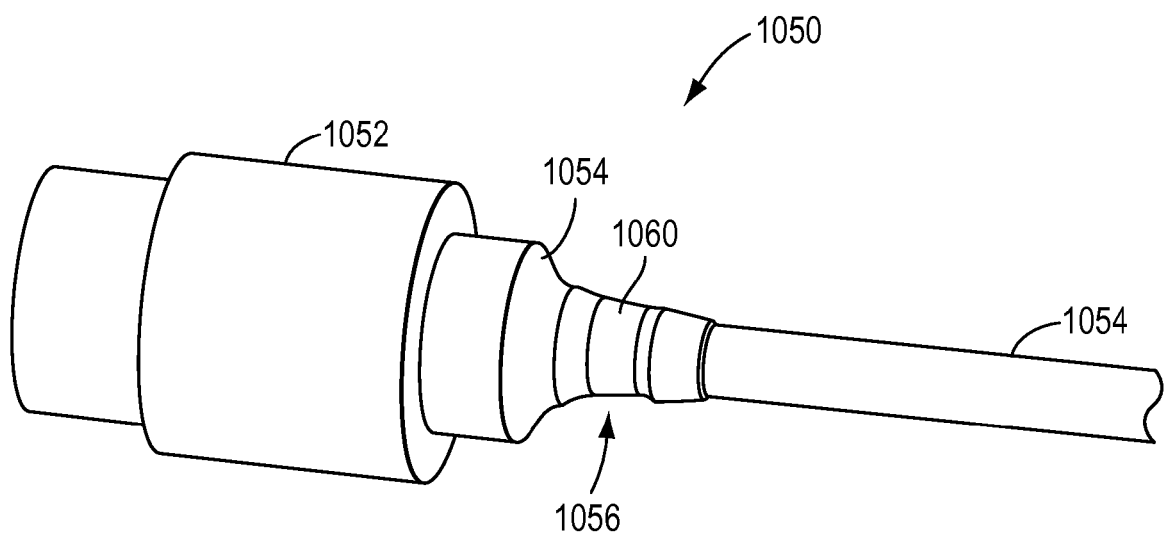
FIG. 12 is a perspective view of a cannula, according to another exemplary embodiment.

In another exemplary embodiment, a cannula 1050 may include a single, continuous, circumferential depression 1056, as shown in FIG. 12. Cannula 1050 may include a bowl portion 1052 and a tube portion 1020, with bowl portion 1052 including a distal bowl section 1054 having a depression 1056 of reduced wall thickness (e.g., in comparison to parts of distal bowl section 1054 not including depression 1056, such as parts of distal bowl section 1052 proximal and/or distal to depression 1056) in which a weld 1060 is located to join bowl portion 1052 and tube portion 1054. Weld 1060 may be a single, continuous circumferential weld, as shown in the exemplary embodiment of FIG. 12. However, depression 1056 is not limited to a single weld 1060 but instead may comprise a plurality of discrete welds 1040 spaced apart from one another, as shown in the exemplary embodiment of FIG. 11.

Cannulas of the various exemplary embodiments described herein may be manufactured according to various procedures. For example, a cannula may be assembled from a plurality of parts. The various exemplary embodiments described herein may be used to manufacture cannulas having a straight tube section or cannulas having a curved tube section. The various exemplary embodiments described herein may also be used with cannulas of different sizes and shapes, such as, for example, cannulas for different instruments, cannulas having different bowl sizes, different bowl shapes, and different tube portion diameters. Further, a bowl portion of a cannula may vary in shape, depending upon the manner by which a cannula is mounted to a cannula mount (e.g., cannula mount 124 of patient side cart 100 of FIG. 1). For example, a bowl portion of a cannula may be connected to a cannula mount via arms of the cannula mount clamping about the bowl portion. In another example, a bowl portion of a cannula may include a projection (not shown), which is inserted into, and clamped by, a cannula mount.

Figure 13:
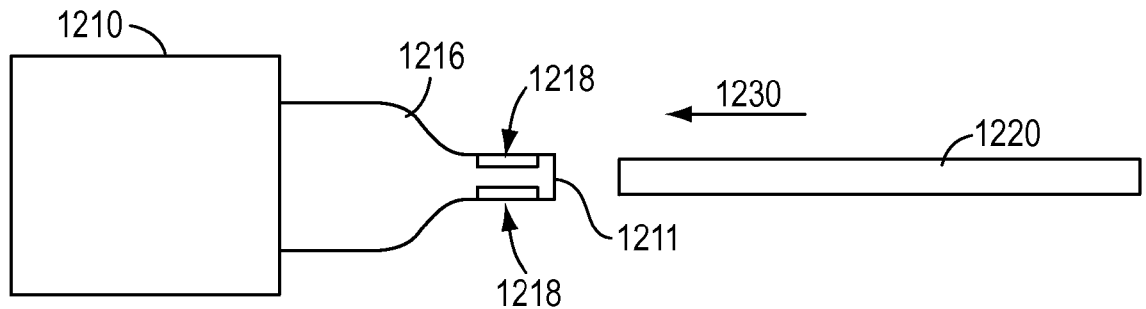
FIG. 13 shows providing a bowl portion and a tube portion in a method of manufacturing a cannula, according to an exemplary embodiment.
Figure 14:
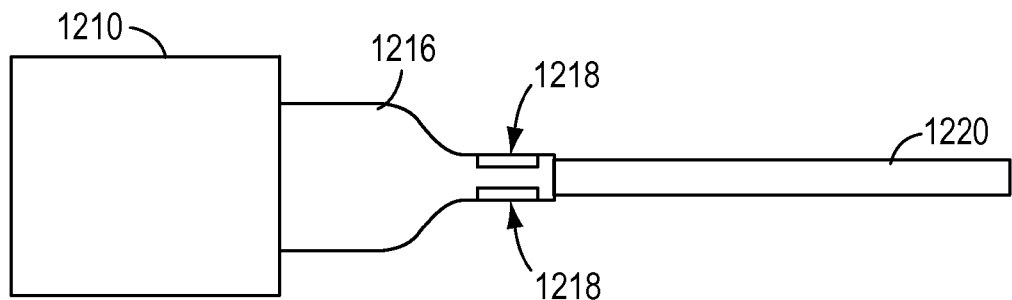
FIG. 14 shows assembling a bowl portion and a tube portion in a method of manufacturing a cannula, according to an exemplary embodiment.
Figure 15:
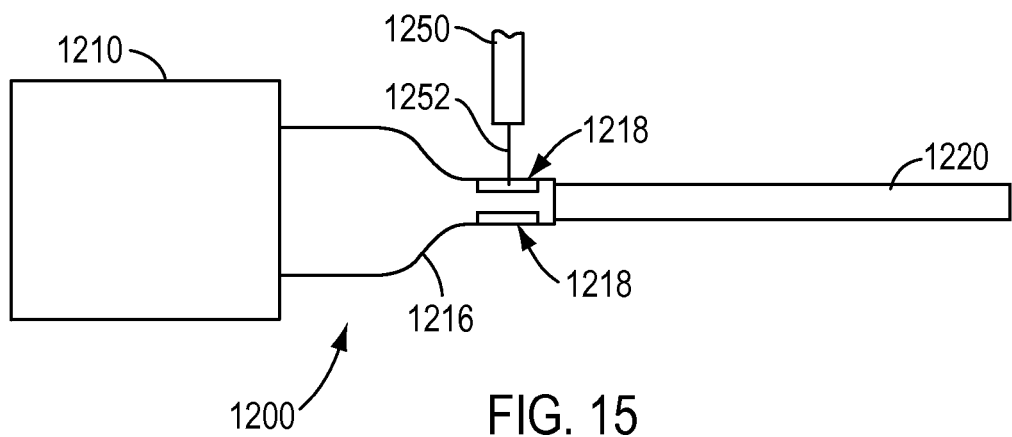
FIG. 15 shows joining a bowl portion and a tube portion in a method of manufacturing a cannula, according to an exemplary embodiment.

A method of manufacturing a cannula will now be described with reference to the schematic exemplary embodiment of FIGS. 13-15. As shown in FIG. 13, a bowl portion 1210 and a tube portion 1220 are separately provided, as described and shown in various exemplary embodiments herein. Tube portion 1210 may be straight, as indicated in FIGS. 13-15 or may include a curved portion. Bowl portion also may have a variety of the shapes, as shown and described herein. Bowl portion 1210 may include a distal bowl section 1216 having a plurality of depressions 1218, as shown in FIGS. 13-15, or bowl portion 1210 may instead have a circumferential section 1015 or depression 1056, as shown in the exemplary embodiment of FIGS. 11 and 12. Tube portion 1220 may be inserted into bowl portion 1210 along direction 1230 in FIG. 13, such as into a distal opening 1211 of bowl portion 1210, to provide the intermediate assembly of bowl portion 1210 and tube portion 1220 shown in FIG. 14.

According to an exemplary embodiment, tube portion 1220 and bowl portion 1210 may have shapes and sizes so that tube portion 1210 and bowl portion 1210 are press fit to one another when assembled in the configuration shown in FIG. 14. This may prevent tube portion 1220 from sliding out of bowl portion 1210 prior to welding. For instance, a distal end 626 of tube portion 620 is inserted into bowl portion 610 past depressions 618, as shown in the exemplary embodiment of FIGS. 6 and 7. The press fit between bowl portion 1210 and tube portion 1220 may facilitate tube portion 1220 remaining within bowl portion 1210 even when a weld between bowl portion 1210 and tube portion 1220 fails or material of bowl portion 1210 and/or tube portion 1220 within a heat affected zone (HAZ) adjacent to a weld fails, such as distal or proximal to weld 640 in the exemplary embodiment of FIG. 6. As a result, even if a weld fails during a surgical procedure, such as due to overloading when extreme forces are applied to a cannula, it may be possible for the bowl portion and tube portion of the cannula to remain connected, such as until the surgical procedure is completed. Thus, the press fit between bowl portion 1210 and tube portion 1220 may facilitate a robust connection between bowl portion 1210 and tube portion 1220, such if a weld between bowl portion 1210 and tube portion 1220 fails.

Once tube portion 1220 has been inserted into bowl portion 1210, tube portion 1220 and bowl portion 1210 are joined to one another. As discussed above, bowl portion 1210 and tube portion 1220 of a cannula may each be made of metal. Thus, one method of joining the parts is via a welding process. However, the bowl portion and tube portion may be made of plastic, as discussed above, and may be joined according to the exemplary embodiments described herein. According to an exemplary embodiment, a welding process may be used to produce discrete welds (not shown), such as within depressions 1218, to weld bowl portion 1210 to tube portion 1220. As depicted in the exemplary embodiment of FIG. 15, a laser source 1250 may be positioned to supply a laser beam 1252 within depressions 1218 to form discrete penetration welds within depressions 1218, as described above with regard to the exemplary embodiment of FIG. 7. The various exemplary embodiments described herein are not limited to welds formed via laser welding, however, and may be formed by other welding processes, such as, for example tungsten inert gas (TIG) welding, metal inert gas (MIG) welding, resistance welding, friction welding, and other welding processes. After welding has been completed, bowl portion 1210 and/or tube portion 1220 may undergo further processing, as may be required, to provide a finished cannula 1200.

By providing a cannula and methods of manufacturing cannulas according to the various exemplary embodiments described herein, a cannula may include a weld having relatively high strength that joins a bowl portion and tube portion of the cannula. Further, various weld configurations in accordance with exemplary embodiments described herein also may provide an intact cannula assembly (e.g., tube portion and bowl portion assembly) configuration able to complete a surgical procedure even in event of a weld failure.

Further modifications and alternative embodiments will be apparent to those of ordinary skill in the art in view of the disclosure herein. For example, the devices, systems, and methods may include additional components or steps that were omitted from the diagrams and description for clarity of operation. Accordingly, this description is to be construed as illustrative only and is for the purpose of teaching those skilled in the art the general manner of carrying out the present disclosure. It is to be understood that the various embodiments shown and described herein are to be taken as exemplary. Elements and materials, and arrangements of those elements and materials, may be substituted for those illustrated and described herein, parts and processes may be reversed, and certain features of the present teachings may be utilized independently, all as would be apparent to one skilled in the art after having the benefit of the description herein. Changes may be made in the elements described herein without departing from the scope of the present disclosure and following claims.

It is to be understood that the particular examples and embodiments set forth herein are non-limiting, and modifications to structure, dimensions, materials, and methodologies may be made without departing from the scope of the present disclosure.

Other embodiments in accordance with the present disclosure will be apparent to those skilled in the art from consideration of the specification and practice of the invention disclosed herein. It is intended that the specification and examples be considered as exemplary only, with being entitled to their full breadth of scope, including equivalents by the following claims.

What is claimed is:

1. A surgical instrument cannula, comprising:
    a bowl portion comprising a distal section having at least one depression in an outer surface of the distal section;
    wherein the distal section of the bowl portion has a reduced wall thickness at a location of the at least one depression;
    a tube portion received by and extending from the distal section, the tube portion being dimensioned to receive a teleoperated surgical instrument; and
    a plurality of welds located at the at least one depression and joining the bowl portion to the tube portion;
    wherein the plurality of welds are discrete welds spaced from one another along a circumferential direction of the surgical instrument cannula.

2. The surgical instrument cannula of claim 1, wherein the at least one depression comprises a plurality of discrete depressions, wherein a differing one of the plurality of welds is located within each of the depressions.

3. The surgical instrument cannula of claim 1, wherein the plurality of welds penetrate about one third of a wall thickness of the tube portion.

4. The surgical instrument cannula of claim 1, wherein the tube portion is straight.

5. The surgical instrument cannula of claim 1, wherein the tube portion has a curved longitudinal axis along at least a part of a length of the tube portion.

6. The surgical instrument cannula of claim 1, wherein the at least one depression has a generally elongated shape along an axial direction of the surgical instrument cannula.

7. The surgical instrument cannula of claim 1, wherein the plurality of welds are spaced from a distal end of the bowl portion along an axial distal-proximal direction of the surgical instrument cannula.

8. The surgical instrument cannula of claim 1, wherein a proximal end region of the tube portion and the bowl portion are press fit to one another.

9. The surgical instrument cannula of claim 1, wherein the bowl portion is configured to be connected to a cannula mount of a surgical system.

10. The surgical instrument cannula of claim 1, wherein the bowl portion further comprises a plurality of ribs having a greater wall thickness than the at least one depression.

11. The surgical instrument cannula of claim 10, wherein the at least one depression comprises a plurality of discrete depressions, wherein the plurality of ribs and the plurality of discrete depressions are alternatingly disposed in circumferential direction around the distal section.

12. A surgical instrument cannula, comprising:
   a bowl portion comprising a proximal end and a distal end;
   a tube portion comprising a proximal end region received in the distal end of the bowl portion, the tube portion being dimensioned to receive a teleoperated surgical instrument; and
   a plurality of discrete welds spaced along a circumferential direction of the surgical instrument cannula joining the bowl portion to the tube portion, wherein the plurality of discrete welds are spaced from the distal end of the bowl portion.

13. The surgical instrument cannula of claim 12, wherein the tube portion is straight.

14. The surgical instrument cannula of claim 12, wherein the tube portion has a curved longitudinal axis along at least a part of the length of the tube portion.

15. The surgical instrument cannula of claim 12, wherein the plurality of discrete welds penetrate about one third of a wall thickness of the tube portion.

16. The surgical instrument cannula of claim 12, wherein the proximal end region of the tube portion and the bowl portion are press fit to one another.

17. The surgical instrument cannula of claim 12, wherein the bowl portion is configured to be connected to a cannula mount of a surgical system.

18. The surgical instrument cannula of claim 12, wherein the bowl portion comprises a circumferential section having a reduced wall thickness in comparison to a remainder of the bowl portion.

19. The surgical instrument cannula of claim 18, wherein the plurality of discrete welds are located in the circumferential section.

20. The surgical instrument cannula of claim 12, wherein the bowl portion comprises at least one depression where the bowl portion has a reduced wall thickness in comparison to a portion of the bowl portion where the at least one depression is not located.

21. The surgical instrument cannula of claim 20, wherein the at least one depression has an elongated shape along an axial direction of the surgical instrument cannula.

22. The surgical instrument cannula of claim 20, wherein:
   the at least one depression comprises a plurality of depressions;
   the bowl portion and tube portion are joined by the plurality of discrete welds positioned at corresponding depressions of the plurality of depressions.

23. The surgical instrument cannula of claim 22, wherein the bowl portion further comprises a plurality of ribs, wherein each rib of the plurality of ribs is between two corresponding depressions of the plurality of depressions.

* * * * *